United States Patent
Lindner

(10) Patent No.: US 11,174,463 B2
(45) Date of Patent: Nov. 16, 2021

(54) METHOD FOR THE PRODUCTION OF HAIR FOLLICLES AND DE NOVO PAPILLAE, AND USE THEREOF FOR IN VITRO TESTS AND IN VIVO IMPLANTS

(71) Applicant: TECHNISCHE UNIVERSITÄT BERLIN, Berlin (DE)

(72) Inventor: Gerd Lindner, Berlin (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 702 days.

(21) Appl. No.: 15/776,359

(22) PCT Filed: Nov. 14, 2016

(86) PCT No.: PCT/EP2016/077541
§ 371 (c)(1),
(2) Date: May 15, 2018

(87) PCT Pub. No.: WO2017/084999
PCT Pub. Date: May 26, 2017

(65) Prior Publication Data
US 2020/0255799 A1    Aug. 13, 2020

(30) Foreign Application Priority Data

Nov. 17, 2015   (DE) .................... 10 2015 119 880.0

(51) Int. Cl.
*C12N 5/071*   (2010.01)

(52) U.S. Cl.
CPC ......... *C12N 5/0627* (2013.01); *C12N 5/0698* (2013.01); *C12N 2502/1323* (2013.01)

(58) Field of Classification Search
None
See application file for complete search history.

(56) References Cited

U.S. PATENT DOCUMENTS

| | | | |
|---|---|---|---|
| 8,841,124 B2 | 9/2014 | Linder et al. | |
| 9,764,064 B2 * | 9/2017 | Lindner | A61L 27/3804 |
| 2010/0197019 A1 * | 8/2010 | Toyoshima | C12N 5/0627 435/377 |
| 2011/0305671 A1 * | 12/2011 | Armani | A61K 38/1858 424/93.3 |
| 2013/0212724 A1 * | 8/2013 | Yoshida | C12N 5/0628 800/18 |
| 2014/0370070 A1 | 12/2014 | Linder et al. | |

FOREIGN PATENT DOCUMENTS

| | | | | |
|---|---|---|---|---|
| CN | 102027106 A | | 4/2011 | |
| EP | 2 105 499 A1 | | 9/2009 | |
| EP | 2105499 | * | 9/2009 | ............... C12N 5/08 |
| WO | WO 03/068248 | * | 8/2003 | ............. A61K 35/36 |
| WO | WO 06/057542 | * | 6/2006 | ............... C12N 5/06 |
| WO | 2007/100870 A2 | | 9/2007 | |
| WO | 2012/163974 A1 | | 12/2012 | |

OTHER PUBLICATIONS

Lin et al, Biotechnology Journal, 2008, 3, 1172-1184. (Year: 2008).*
Gerd Lindner et al., "De novo formation and ultra-structual characterization of a fiber-producing human hair follicle equivalent in vitro", Journal of Biotechnology, vol. 152, No. 3, Jan. 21, 2011.
International Search Report dated Dec. 7, 2016, dated Dec. 19, 2016.
English Translation of International Search Report dated Dec. 7, 2016, dated Dec. 19, 2016.
Chinese Office Action dated Jun. 2, 2021, in connection with Chinese Application No. 201680078151.6.

* cited by examiner

*Primary Examiner* — Allison M Fox
(74) *Attorney, Agent, or Firm* — Norris McLaughlin, P.A.

(57) ABSTRACT

The present invention describes a method for producing de novo papillae comprising the steps of a) providing isolated dermal papilla fibroblasts (DPF) from at least one dermal papilla (DP) from at least one hair follicle, b) providing isolated connective tissue sheath fibroblasts (CTSF) from at least one hair follicle and c) co-culturing the DPF with the CTSF under substantially non-adherent cell culture conditions to form spheroid cell aggregates.

15 Claims, 3 Drawing Sheets

Figure 1:
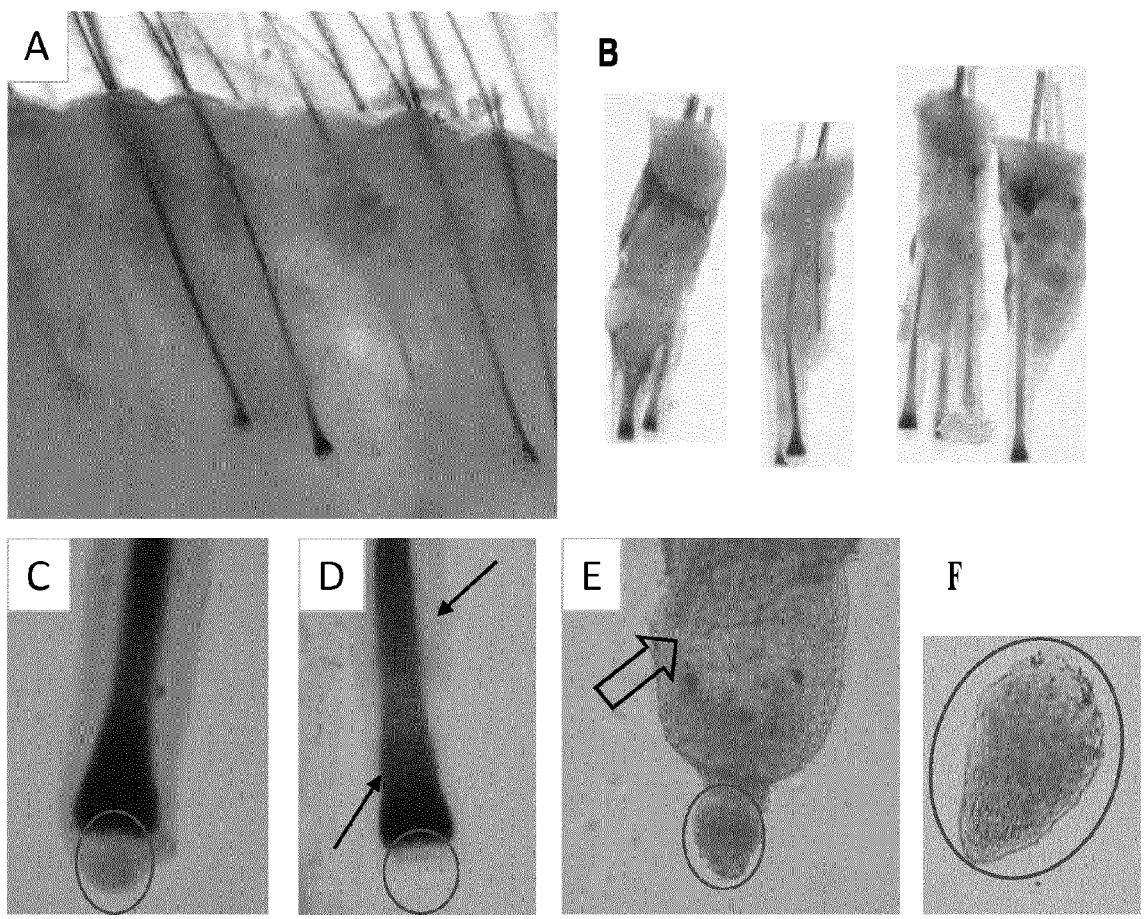

METHOD FOR THE PRODUCTION OF HAIR FOLLICLES AND DE NOVO PAPILLAE, AND USE THEREOF FOR IN VITRO TESTS AND IN VIVO IMPLANTS

This application is the U.S. National Stage of International Application No. PCT/EP2016/077541, filed Nov. 14, 2016, which claims foreign priority benefit under 35 U.S.C. § 119 of German Application No. 10 2015 119 880.0 filed Nov. 17, 2015.

Genetically determined hair loss, also known by the name androgenetic alopecia, is a very widespread clinical picture with psychological and emotional effects and has a considerable impact on the everyday lives of those affected in our society. Genetically determined hair loss is considered to be caused by hypersensitivity of the hair follicles to the steroid hormone dihydrotestosterone.

In addition to drug treatment of androgenetic alopecia, another option is hair transplantation which, to date, still provides by far the best cosmetic results. Transplantation involves redistributing intact androgen-insensitive hair follicles from the occipital nape region or lateral temple region to the crown or frontal region of a balding head.

While modern hair transplantation techniques are becoming ever more sophisticated and effective, there is naturally, in particular where hair loss has progressed considerably, not enough donor hair available to be able to achieve an adequate, cosmetically significant hair density and thus a satisfactory treatment result. Carrying out a hair transplantation requires suitable hair transplants or cells as the material which is used on the recipient. Multiplying the necessary cells generally takes a number of weeks. Furthermore, multiplication must take place under clean room conditions, which means that the product is classed as an ATMP (Advanced Therapeutic Medicinal Product) which has to clear extremely high barriers to development and market entry.

The object of the present invention is to reduce or avoid one or more disadvantages of the prior art. In particular, one object of the present invention is to provide a method with which de novo papillae or hair follicles can be produced.

The present invention achieves this object by providing a method for producing de novo papillae comprising the steps of: a) providing isolated dermal papilla fibroblasts (DPF) from at least one dermal papilla (DP) from at least one hair follicle; b) providing isolated connective tissue sheath fibroblasts (CTSF) from at least one hair follicle; and c) co-culturing the DPF with the CTSF under substantially non-adherent cell culture conditions to form spheroid cell aggregates.

It has surprisingly been found that de novo papillae can be produced from mixtures of at least DPF and CTSF. In comparison with methods known from the prior art for multiplying hair follicles, the production method according to the invention can be carried out in a shorter time. It is accordingly possible within one day to obtain cell populations from hair follicles, to use these cells to produce de novo papillae and/or hair follicles in a larger number and to implant these newly generated de novo papillae or hair follicles into the hairless scalp to be treated, such that new hair can again be formed at these sites.

Unless otherwise unambiguously indicated by the context, the use of singular or plural forms always includes both the singular and the plural.

The method according to the invention relates to the production of de novo papillae. The terms "de novo papilla", "neopapilla" or "spheroid" are used synonymously and designate a substantially spheroid cell aggregate of dermal papilla fibroblasts (DPF) and connective tissue sheath fibroblasts (CTSF). The de novo papilla thus comprises a mixture of at least DPF and CTSF. The de novo papillae consist of approx. 2 to 20000 cells, preferably of 10 to 15000, particularly preferably of 500 to 10000, very particularly preferably of 1000 to 5000 cells. The de novo papilla is preferably at least half the size of a physiological dermal papilla (DP) of a hair follicle after isolation thereof. The de novo papilla likewise preferably has roughly the shape of a physiological DP of a hair follicle after isolation thereof.

The de novo papilla may comprise a coating which contains one or more different extracellular matrix proteins such as for example collagen IV, fibronectin and/or laminin. This coating may be created by the DPF and CTSF themselves while they are forming the de novo papilla. Alternatively or additionally thereto, the de novo papilla can also be coated during and/or after the formation thereof by further addition of one or more different extracellular matrix proteins to the culture medium.

The production method of the present invention is carried out in vitro. "In vitro" is taken to mean any environment which is not located within a living organism, for example a human or animal body. The in vitro detection method according to the invention thus explicitly does not include a method which is carried out on a human or animal body.

In the method according to the invention, isolated dermal papilla fibroblasts (DPF) from at least one dermal papilla (DP) are provided in a first method step a), wherein the DP originates from at least one hair follicle.

The DP can be provided from the hair follicle and the DPF isolated from the DP for example as follows: isolated hair follicles are immobilized on the hair shaft, for example with a pair of forceps, and the connective tissue sheath is separated diametrically from the hair shaft, for example with another pair of forceps, so everting the bulb and thus exposing the DPF and the hair shaft with the hair matrix. In this way, the DP can be separated from the remaining part of the hair follicle, which may be achieved for example with the aid of a needle or cannula.

The isolated DP are then for example transferred into a cell culture vessel and mechanically immobilized on the surface of the cell culture vessel. The DPF are preferably obtained in that the isolated DP are mechanically held down on the bottom of the cell culture vessel, for example by means of a needle tip or a scalpel. The morphology of the DP is largely retained here, but the basal lamina of the DP is slightly perforated, such that the DPF can migrate out of the DP. The DPF can also be obtained from the DP with the aid of enzymatic or non-enzymatic separation.

After being isolated and prior to being used in the method according to the invention, the DPF may be subjected to intermediate culturing, for example to multiply their number. The DPF used in the method according to the invention may accordingly be descendants or clones of the originally isolated DPF.

The hair follicles from which the DP and DPF are isolated originate from tissue. Methods for removing hair follicles from tissue are known to a person skilled in the art. The hair follicles are preferably removed from the tissue in accordance with good medical practice. The hair follicles are preferably removed from the tissue in such a way that they remain substantially intact, i.e. undamaged. The hair follicles can for example be removed from the tissue as follows by: i) separating the epidermis from the underlying dermis or adipose tissue in the tissue, preferably using a scalpel; ii) dissecting out hairs from the dermis or the adipose tissue of the tissue. The removed hairs comprise the hair follicles at their proximal ends. Prior to step ii), the dermis or the adipose tissue may optionally be compressed to facilitate subsequent dissecting out of the hair follicles present therein. Compression may here for example be carried out with the aid of a pair of forceps. The hair follicles are preferably removed under a microscope. The hair follicles are preferably obtained from punch biopsies which preferably consist of individual follicular units (FU). A follicular unit is the name for a group of 1-4 hair follicles which grow spatially packed closely together, are surrounded by a tissue capsule and moved by a common muscle (arrector pili muscle). The follicular units are obtained either by dissection under a stereo microscope from a previously taken strip of scalp or more precisely by direct puncture of the scalp by means of a cannula. The latter method is known as Follicular Unit Extraction (FUE).

The tissue from which the hair follicles may be obtained, for example for isolating the DP or DPF, originates from a mammal. This mammal may be a human, monkey, pig, dog, cat or rodent, preferably a human. The mammal is thus a donor for the tissue containing the hair follicles. The mammal is particularly preferably a human patient suffering from hair loss.

The tissue preferably comprises skin. The tissue may here be obtained from any hairy region of the body, preferably from the head, chest, eyebrows, beard, genital area, leg or other regions of the body. The tissue is particularly preferably taken from a region of the body which is located in the vicinity of the body part affected by hair loss. For example, if the hair loss concerns the crown, i.e. the part of the head located between the forehead and the back of the head, the tissue may preferably be taken from the nape or temple regions of the head. The tissue is preferably obtained by means of a biopsy.

Before the hair follicles are removed from the tissue, for example for isolating the DP or DPF, said tissue may be subjected to one or more cleaning steps in order to remove from the tissue any interfering substances which may be present.

Step b) of the method according to the invention involves providing isolated connective tissue sheath fibroblasts (CTSF) from at least one hair follicle.

The CTSF can be provided from the hair follicles for example as follows: isolated hair follicles are immobilized on the hair shaft, for example with a pair of forceps, and the connective tissue sheath is separated diametrically from the hair shaft, for example with another pair of forceps, so everting the bulb. In this way, the proximal part of the bulb with the CTSF can be separated from the remaining part of the hair follicle, which may be achieved for example with the aid of a needle or cannula.

The isolated connective tissue sheath is then for example transferred into a cell culture vessel and mechanically immobilized on the surface of the cell culture vessel. The CTSF are preferably obtained in that the isolated connective tissue sheath is mechanically held down on the bottom of the cell culture vessel, for example by means of a needle tip or a scalpel. The morphology of the connective tissue sheath is largely retained here, but the connective tissue is slightly perforated, such that the CTSF can migrate out of the connective tissue. The CTSF can preferably also be obtained from the connective tissue with the aid of enzymatic or non-enzymatic separation.

After being isolated and prior to being used in the method according to the invention, the CTSF may be subjected to intermediate culturing, for example to multiply their number. The CTSF used in the method according to the invention may accordingly be descendants or clones of the originally isolated DPF.

The hair follicles from which the CTSF are isolated originate from tissue. Methods for removing hair follicles from tissue are known to a person skilled in the art. The hair follicles are preferably removed from the tissue in accordance with good medical practice. The hair follicles are preferably removed from the tissue in such a way that they remain substantially intact, i.e. undamaged. The hair follicles can for example be removed from the tissue as follows by: i) separating the epidermis from the underlying dermis or adipose tissue in the tissue, preferably using a scalpel; ii) dissecting out hairs from the dermis or the adipose tissue of the tissue. The removed hairs comprise the hair follicles at their proximal ends. Prior to step ii), the dermis or the adipose tissue may optionally be compressed to facilitate subsequent dissecting out of the hair follicles present therein. Compression may here for example be carried out with the aid of a pair of forceps. The hair follicles are preferably removed under a microscope.

The tissue from which the hair follicles may be obtained, for example for isolating the CTSF, originates from a mammal. This mammal may be a human, monkey, pig, dog, cat or rodent, preferably a human. The mammal is thus a donor for the tissue containing the hair follicles. The mammal is particularly preferably a human patient suffering from hair loss.

The tissue preferably comprises skin. The tissue may here be obtained from any hairy region of the body, preferably from the head, chest, eyebrows, beard, genital area, leg or other regions of the body. The tissue is particularly preferably taken from a region of the body which is located in the vicinity of the body part affected by hair loss. For example, if the hair loss concerns the crown, i.e. the part of the head located between the forehead and the back of the head, the tissue may preferably be taken from the nape or temple regions of the head. The tissue is preferably obtained by means of a biopsy.

Before the hair follicles are removed from the tissue, for example for isolating the CTSF, said tissue may be subjected to one or more cleaning steps in order to remove from the tissue any troublesome substances which may be present.

The DPF and CTSF are thus obtained from isolated hair follicles. The DPF and CTSF may here be obtained from the same hair follicle. The DPF and CTSF may, however, also be obtained from different hair follicles. If the DPF and CTSF are obtained from different hair follicles, these hair follicles may have been isolated from the same tissue, for example from tissue which was for example taken from the nape region of a donor's head. If the DPF and CTSF are obtained from different hair follicles, these hair follicles may also have been isolated from different tissues, such that for example one of the tissues was for example taken from the nape region of a donor's head while the other tissue was for example taken from a donor's beard. The donor may be the same or a different donor. If it is a different donor, said donor is preferably an allogeneic donor. It is preferably the same, i.e. autologous, donor.

The following step c) of the method according to the invention involves co-culturing the DPF and CTSF under substantially non-adherent cell culture conditions to form spheroid cell aggregates.

The expression "non-adherent cell culture conditions" is taken for the purposes of the method according to the invention to mean cell culture conditions in which the cells have substantially no direct and/or continuous contact with the surface of the cell culture vessel. This may, for example, be achieved by the surfaces of the cell culture vessel consisting of a material and/or having an anti-adhesion coating which reduces or substantially prevents the cells from adhering. Suitable culture vessels and/or coatings for these cell culture vessels are known to a person skilled in the art. Such non-adherent cell culture vessels may for example be manufactured from glass or polystyrene. The surfaces of the cell culture vessel are preferably coated with contact-inhibiting materials such as PTFE, poly-HEMA, agarose or fluorocarbon solutions.

According to the invention, the definition of non-adherent cell culture conditions likewise includes the "hanging drop" culture method, in which the cells are located within a drop of nutrient medium. The surface tension of the liquid keeps the drop in a hanging position on the surface of the cell culture vessel and encloses the cells located therein. Under the effect of gravity, the cells accumulate in the lower part of the drop and have substantially no direct contact with the culture vessel. Within the drop, the cells can form into spheroids.

Co-culturing of the DPF and CTSF gives rise to substantially spheroid cell aggregates which are similar to physiological DP in terms of shape and size.

The DPF and CTSF may be co-cultured in an identical or different ratio. The DPF and CTSF are preferably co-cultured in a ratio of 1-20:1-20, preferably 1-10:1-10, particularly preferably 1-5:1-5, very particularly preferably 1-2.5:1-2.5, in particular preferably 1:1.

In one embodiment, a cell concentration of 2 to 20000 DPF+CTSF/mm$^2$ of the cell culture vessel, preferably 10 to 15000, particularly preferably 500 to 10000, very particularly preferably 1000 to 5000 is selected for co-culturing the DPF and CTSF in step c).

Co-culturing of the DPF and CTSF takes place in cell culture vessels, suitable cell culture vessels being known to a person skilled in the art. Said cell culture vessels may for example be commercially obtainable cell culture plates, dishes or flasks. The cell culture vessels may have one or more cavities. Co-culturing of the DPF and CTSF preferably takes place in a cavity of a cell culture vessel. The cell culture vessels may be "multiwall" plates with more than one cavity. The cell culture vessels preferably have 2 to 10000 cavities, particularly preferably 4 to 1536, very particularly preferably 6 to 384.

The bottoms of the cell culture vessel cavities may be planar or non-planar. The cavities are preferably round-bottomed. Cavities which are funnel-shaped are likewise preferred.

In one embodiment, the DPF and CTSF are sedimented on the bottom of the cell culture vessels by centrifugation prior to being co-cultured in step c). This initial concentration of the DPF and CTSF on the bottom of the cell culture vessel means the cell aggregates are formed more rapidly.

Co-culturing of the DPF and CTSF takes place for at least 1 min, preferably for 10 min to 14 days, particularly preferably for 20 min to 48 h, very particularly preferably for 30 min to 24 h, in particular preferably for 1 h to 4 h.

Co-culturing of the DPF and CTSF in step c) of the method according to the invention preferably takes place in the presence of blood plasma and/or blood serum. The blood plasma and/or blood serum is preferably human blood plasma and/or blood serum, preferably autologous blood plasma and/or blood serum. The blood plasma and/or blood serum is preferably 1-100% blood plasma or blood serum, preferably 15-75%, particularly preferably 30-50%.

Co-culturing of the DPF and CTSF in step c) of the method according to the invention may take place under substantially static conditions or with agitation. Co-culturing preferably takes place with rotating, swiveling or shaking agitation.

Still further cell types may additionally be present during co-culturing of the DPF and CTSF in step c) of the method according to the invention. Endothelial cells (EC) and/or cells of stromal vascular fractions (SVF) are preferably additionally present during the co-culturing.

Methods for obtaining the EC are known to a person skilled in the art. The EC may be obtained from blood vessels, preferably from blood vessels which are located on or in hair follicles. The EC are preferably obtained from a human donor. The EC are particularly preferably autologous. After being isolated and prior to being used in the method according to the invention, the EC may be subjected to intermediate culturing, for example to multiply their number. The EC used in the method according to the invention may accordingly be descendants or clones of the originally isolated EC. Due to the presence of EC during co-culturing of the DPF with the CTSF in step c) of the method according to the invention, de novo papillae which comprise DPF, CTSF and EC are created. Such de novo papillae, or hair follicles generated therefrom, may be introduced into the skin of a mammal for treating a condition involving a reduced quantity of hair. Once transplanted into the skin, such de novo papillae or hair follicles generated therefrom enable accelerated formation of blood vessels on the papillae or hair follicles and thus an improved rate of formation or growth of the hair arising therefrom.

Methods for obtaining the SVF are known to a person skilled in the art. The SVF may for example be obtained by excising adipose tissue or by liposuction. The SVF is preferably obtained from a human donor; it is particularly preferably an autologous SVF. The SVF comprises various cell populations such as precursors of adipocytes (preadipocytes), endothelial cells, endothelial muscle cells, fibroblasts, macrophages or blood cells. After obtaining the SVF from the donor, specific components of the SVF can be removed from the SVF, which removal may proceed by one or more washing, cleaning or isolation steps or also by targeted separation or removal of the components. After being isolated and prior to being used in the method according to the invention, the SVF may likewise be subjected to intermediate culturing, for example to multiply their number. The SVF used in the method according to the invention may accordingly be descendants or clones of the originally isolated SVF. Thanks to the presence of the SVF during co-culturing in step c) of the method according to the invention, elevated or faster rapid cell multiplication of the DPF and CTSF is achieved and formation of the de novo papillae is accordingly accelerated.

The further cell types may be present in an identical or a different ratio to the DPF and CTSF. The DPF, CTSF and EC or SVF are preferably co-cultured in a ratio of 1-20:1-20:1-20, preferably 1-10:1-10:1-10, particularly preferably 1-5:1-5:1-5, very particularly preferably 1-2.5:1-2.5:1-2.5, in particular preferably 1:1:1. If the DPF and CTSF are cultured together with EC and SVF, co-culturing preferably proceeds in a ratio of 1-20:1-20:1-20:1-20, preferably 1-10:1-10:1-10:1-10, particularly preferably 1-5:1-5:1-5:1-5, very particularly preferably 1-2.5:1-2.5:1-2.5:1-2.5, in particular preferably 1:1:1:1.

During the creation of the de novo papilla, a layer of extracellular matrix proteins generally forms in and/or around the cell aggregate, which layer is generally formed by the DPF and/or CTSF. Alternatively or additionally thereto, the de novo papilla may be coated with extracellular matrix proteins during and/or after step c) of the method according to the invention. This may, for example, be achieved by a composition comprising these extracellular matrix proteins additionally being added to the culture medium in order to facilitate and/or accelerate the creation of this papilla coating. It is likewise possible for the de novo papillae first to be separated from the culture medium and then combined with a composition comprising these extracellular matrix proteins. This composition of the added extracellular matrix proteins preferably comprises collagen IV, fibronectin and/or laminin. This composition of the additionally added extracellular matrix proteins preferably comprises or consists of collagen IV, fibronectin and laminin, preferably in a ratio of 2-6:0.5-2:0.5-2 parts by weight, particularly preferably in a ratio of 3-5:0.5-1.5:0.5-1.5 parts by weight, very particularly preferably in a ratio of 4:1:1.15 parts by weight. The composition of the extracellular matrix proteins may also be used in combination with other matrices. In one embodiment, the composition of the extracellular matrix proteins furthermore comprises other collagens (such as for example collagen I, collagen 10 A1, collagen 18 A1), glycosaminoglycans and/or proteoglycans, preferably heparan sulfates, decorin, keratan sulfates, biglycan, aggrecan, versican, perlecan, osteopontin, CD44v3 and/or syndecan.

The de novo papilla is preferably coated with these matrix proteins by addition of extracellular matrix proteins to the cell culture medium. Coating of the de novo papilla with the extracellular matrix proteins preferably likewise takes place under substantially non-adherent cell culture conditions. Coating of the de novo papilla takes place for at least 1 min, preferably for 10 min to 14 days, particularly preferably for 20 min to 48 h, very particularly preferably for 30 min to 24 h, in particular preferably for 1 h to 4 h.

The present invention also relates to de novo papillae which are produced by the method according to the invention.

In a preferred embodiment, the method for producing de novo papillae comprises the steps of: a) providing isolated DPF from at least one DP from at least one hair follicle; b) providing isolated CTSF from at least one hair follicle; and c) co-culturing the DPF and CTSF and additionally EC under substantially non-adherent cell culture conditions to form spheroid cell aggregates. The DPF, CTSF and EC are preferably co-cultured in a ratio of 1-20:1-20:1-20. The de novo papillae are preferably coated with these matrix proteins by addition of extracellular matrix proteins to the cell culture medium. Co-culturing may take place with rotating, swiveling or shaking agitation. Co-culturing may preferably take place in a cylindrical cavity which preferably has a round bottom. It is possible to carry out co-culturing in multiwell cell culture vessels having for example 96 or 384 wells. Co-culturing can furthermore take place in the presence of blood plasma and/or blood serum. The DPF, CTSF and EC preferably originate from a donor.

In a further preferred embodiment, the method for producing de novo papillae comprises the steps of: a) providing isolated DPF from at least one DP from at least one hair follicle; b) providing isolated CTSF from at least one hair follicle; and c) co-culturing the DPF and CTSF and additionally SVF under substantially non-adherent cell culture conditions to form spheroid cell aggregates. The DPF, CTSF and SVF are preferably co-cultured in a ratio of 1-20:1-20:1-20. The de novo papillae are preferably coated with extracellular matrix proteins. Co-culturing may take place with rotating, swiveling or shaking agitation. Co-culturing can furthermore take place in the presence of blood plasma and/or blood serum. The DPF, CTSF and SVF preferably originate from a donor.

In a further preferred embodiment, the method for producing de novo papillae comprises the steps of: a) providing isolated DPF from at least one DP from at least one hair follicle; b) providing isolated CTSF from at least one hair follicle; and c) co-culturing the DPF, CTSF and additionally EC and SVF under substantially non-adherent cell culture conditions. The DPF, CTSF, EC and SVF are preferably co-cultured in a ratio of 1-20:1-20:1-20:1-20. The de novo papillae are preferably coated with extracellular matrix proteins. Co-culturing may take place with rotating, swiveling or shaking agitation. Co-culturing can furthermore take place in the presence of blood plasma and/or blood serum. The DPF, CTSF, EC and SVF preferably originate from a donor.

The present invention furthermore relates to a method for producing hair follicles comprising the steps of: a) providing at least one de novo papilla produced by the method according to the invention for producing de novo papillae; b) providing at least one further cell population selected from keratinocytes (KC), melanocytes (MC) or connective tissue sheath fibroblasts (CTSF); and c) co-culturing the de novo papilla with the at least one further cell population under substantially non-adherent cell culture conditions.

The "hair follicle" produced with the aid of the method according to the invention denotes a follicle structure which is incomplete in comparison with natural hair follicles, which may comprise a condensed core (papilla) of fibroblasts of mesenchymal origin and an enclosing outer and/or inner epithelial hair root sheath but without containing further cell types or structures such as muscle or nerve cells, blood vessels etc., such that the hair follicle is smaller in size in comparison with natural hair follicles. A hair follicle is composed of a de novo papilla from at least DPF and CTSF which is stably covered or colonized with at least one further cell population selected from keratinocytes (KC), melanocytes (MC) or fibroblasts, such as for example CTSF. A hair follicle is preferably composed of a de novo papilla which is stably covered or colonized with at least one further cell population selected from KC, MC or CTSF, wherein the at least one further cell population may be or is obtained from a hair follicle. The hair follicle has a three-dimensional, optionally spatially delimited shape which is similar to the three-dimensional appearance of a physiological hair follicle. The hair follicles may have a polar structure, for example a pointed projection on one side of the hair follicle, which is reminiscent of the structures in the early morphogenesis of physiological hair follicles.

A first method step a) of the method according to the invention for producing the hair follicles involves providing at least one de novo papilla, wherein the de novo papilla was produced by the previously described method.

Step b) of the method according to the invention for producing the hair follicles involves providing at least one further cell population selected from KC, MC or CTSF.

The following step c) of the method according to the invention for producing the hair follicles involves co-culturing the de novo papilla with the at least one further cell population selected from keratinocytes (KC), melanocytes (MC) or connective tissue sheath fibroblasts (CTSF) under substantially non-adherent cell culture conditions. The KC, MC and/or CTSF need not originate from a hair follicle, but may instead be obtained from other mammalian tissues, such as for example skin. The at least one further cell population may preferably be obtained from a hair follicle and/or is obtained from a hair follicle.

The KC, MC and/or CTSF may be obtained from the same hair follicle. The KC, MC and/or CTSF may, however, also be obtained from different hair follicles. If the KC, MC and/or CTSF are obtained from different hair follicles, these hair follicles may have been isolated from the same tissue, for example from tissue which was for example taken from the nape region of a donor's head. If the KC, MC and/or CTSF are obtained from different hair follicles, these hair follicles may also have been isolated from different tissues, such that for example one of the tissues was for example taken from the nape region of a donor's head while another tissue was for example taken from a donor's beard. In the latter case, the donor may be the same or a different donor. If it is a different donor, said donor is preferably an allogeneic donor. It is preferably the same, i.e. autologous, donor.

The at least one further cell population is particularly preferably obtained from the same hair follicle from which the DP was isolated. After being isolated and prior to being used in the method according to the invention for producing the hair follicles, the KC, MC and/or CTSF may be subjected to intermediate culturing, for example to multiply their number. The KC, MC and/or CTSF used in the method according to the invention may accordingly be descendants or clones of the originally isolated KC, MC and/or CTSF.

The at least one further cell population may be present in an identical or a different ratio to the de novo papilla. The de novo papilla is preferably co-cultured with KC, MC and/or CTSF in a ratio of 1-10:1-50, particularly preferably in a ratio of 1-5:1-40. The de novo papilla is preferably co-cultured with KC and MC, preferably in a ratio of 1-10:1-50:1-50, preferably in a ratio of 1-5:1-20:1-20. The de novo papilla is particularly preferably co-cultured with KC, MC and CTSF, preferably in a ratio of 1-10:1-50:1-50:1-50. The de novo papilla is preferably co-cultured first with the KC and MC, such that the KC and MC form a layer around the de novo papilla and then co-culturing with the CTSF is carried out. The resultant covering with CTSF means that hair follicles are obtained with which improved skin integration can be achieved.

Co-culturing the de novo papilla with at least one further cell population takes place for at least 10 min, preferably for 20 min to 3 weeks, particularly preferably for 30 min to 24 h, very particularly preferably for 1 h to 4 h.

Co-culturing of the de novo papilla with the at least one further cell population in step c) of the method according to the invention for producing the hair follicles can take place under substantially static conditions or with agitation. Co-culturing preferably takes place with rotating, swiveling or shaking agitation.

One preferred embodiment of the method for producing hair follicles comprises the steps of: a) providing at least one de novo papilla produced by the method according to the invention for producing de novo papillae; b) providing KC and MC; and c) co-culturing the de novo papilla with the KC and MC under substantially non-adherent cell culture conditions. The de novo papilla here preferably comprises DPF, CTSF and additionally EC and/or SVF. The de novo papilla is preferably coated with extracellular matrix proteins. The de novo papilla, KC and MC are preferably co-cultured in a ratio of 1-10:1-50:1-50. Co-culturing may take place with rotating, swiveling or shaking agitation. Co-culturing may preferably take place in a cylindrical cavity which preferably has a round bottom. It is possible to carry out co-culturing in multiwell cell culture vessels having for example 96 or 384 wells. Not only the cells for the production of the de novo papilla but also the KC and MC preferably originate from a donor.

A further preferred embodiment of the method for producing hair follicles comprises the steps of: a) providing at least one de novo papilla produced by the method according to the invention for producing de novo papillae; b) providing KC, MC and CTSF; and c) co-culturing the de novo papilla with the KC, MC and CTSF under substantially non-adherent cell culture conditions. The de novo papilla here preferably comprises DPF, CTSF and additionally EC and/or SVF. The de novo papilla is preferably coated with extracellular matrix proteins. The de novo papilla, KC, MC and CTSF are preferably co-cultured in a ratio of 1-10:1-50:1-50:1-50. Co-culturing may take place with rotating, swiveling or shaking agitation. Co-culturing may preferably take place in a cylindrical cavity which preferably has a round bottom. It is possible to carry out co-culturing in multiwell cell culture vessels having for example 96 or 384 wells. Not only the cells for the production of the de novo papilla but also the KC, MC and CTSF preferably originate from a donor.

The present invention moreover comprises hair follicles which are produced by the method according to the invention.

The de novo papillae and/or the hair follicles which were produced by one of the methods according to the invention may be used to produce a skin equivalent. The skin equivalents are preferably produced on the basis of a skin matrix, wherein the skin matrix may for example be an artificial skin matrix such as for example Matriderm® or donor skin. Insertion sites, for example in the form of perforations, for the de novo papillae and/or the hair follicles are introduced into this skin matrix, for example by means of a punch, scalpel or laser. These insertion sites may be introduced into the skin matrix in a regular or irregular spacing from one another. The de novo papillae and/or hair follicles are introduced into the insertion sites of the skin matrix. The present invention accordingly also relates to a skin equivalent which comprises the de novo papilla and/or the hair follicles which were produced by one of the methods according to the invention. The skin equivalent may additionally comprise one or more layers of KC and/or MC, wherein this/these layer(s) are preferably applied over the de novo papillae and/or hair follicles located in the skin equivalent. The skin equivalent may furthermore comprise other cells and/or cell structures such as immune cells (dendritic cells, lymphocytes, etc.), neuronal cells, sebaceous and sweat gland cells/tissue, muscle cells/fibers, vessel structures and further cell types which are present in natural, healthy or diseased skin.

The de novo papillae and/or the hair follicles which were produced by one of the methods according to the invention may be used to produce an implant. The present invention accordingly also relates to an implant which comprises the de novo papillae and/or the hair follicles which were produced by one of the methods according to the invention, optionally together with pharmaceutically acceptable adjuvants.

The present invention moreover comprises a transplant which comprises an effective amount of the skin equivalent optionally together with pharmaceutically acceptable adjuvants.

The present invention also relates to the use of the de novo papilla, of the hair follicles which were produced by the method according to the invention and/or of the skin equivalent comprising the de novo papillae and/or hair follicles for the therapeutic treatment of a condition involving a reduced quantity of hair. For the therapeutic treatment of a condition involving a reduced quantity of hair, it is preferred to produce the de novo papillae and/or hair follicles using allogeneic cells, which means that the donor of the cells used and the recipient of the produced de novo papillae and/or hair follicles belong to the same species, i.e. that both donor and recipient are for example human. It is particularly preferred for the therapeutic treatment of a condition involving a reduced quantity of hair to produce the de novo papillae and/or hair follicles using autologous cells, which means that the donor of the cells used and the recipient of the produced de novo papillae and/or hair follicles are identical, i.e. for example the same human being.

The present invention also relates to the use of the de novo papilla, hair follicles and/or skin equivalents according to the invention for in vitro testing of hair growth-regulating substances.

The present invention furthermore relates to the use of the de novo papilla, hair follicles and/or skin equivalents according to the invention for in vitro testing of substances for toxic characteristics.

The present invention also comprises a kit for carrying out the method according to the invention. To this end, the kit may comprise the de novo papillae, the hair follicles, the skin equivalent, the implant and/or the transplant according to the invention, in order for example to carry out the methods according to the invention for treating a condition involving a reduced quantity of hair or for screening substances. The kit may optionally also include instructions for use of the kit and/or for carrying out the method according to the invention. The kit may furthermore comprise further components for carrying out the method according to the invention, such as for example reaction vessels, filters, solutions and/or other agents.

The present invention moreover comprises a method for treating a condition involving a reduced quantity of hair, wherein the de novo papilla, hair follicles and/or skin equivalents according to the invention are introduced into the skin of a mammal which requires this treatment.

The present invention also relates to a method for in vitro screening of substances with hair growth-regulating characteristics which comprises the following steps: a) providing a sample of the de novo papilla, hair follicles and/or skin equivalent according to the invention; b) dividing the corresponding sample into portions; c) incubating at least one portion with substances which are to be tested; and d) comparing the parameters of the hair characteristics in the portion with another portion which has not been incubated with the substances.

The invention is explained in greater detail below with reference to exemplary embodiments and the associated figures.

FIGURES

FIG. 1 shows:
A) A scalp biopsy which was taken for an FUT hair transplantation and from which the individual hair follicles can be dissected to isolate the cells.
B) Individual follicular units which were taken for an FUE hair transplantation. The individual cell types can likewise be isolated from these units.
C) A proximal hair follicle dissected out of an FU which has subsequently been incised and diametrically everted in order to expose CTS and DP (red circle).
D) A proximal hair follicle after eversion and removal of the CTS with DP. All that remains is the hair shaft with the surrounding epithelial tissue (KC, MC). The red circle indicates the missing DP.
E) CTS tissue envelope which is still joined to the DP and contains CTFS cells and endothelial cells.
F) DP separated from the CTS for further cell dissociation from the tissue structure.

Figure 2:
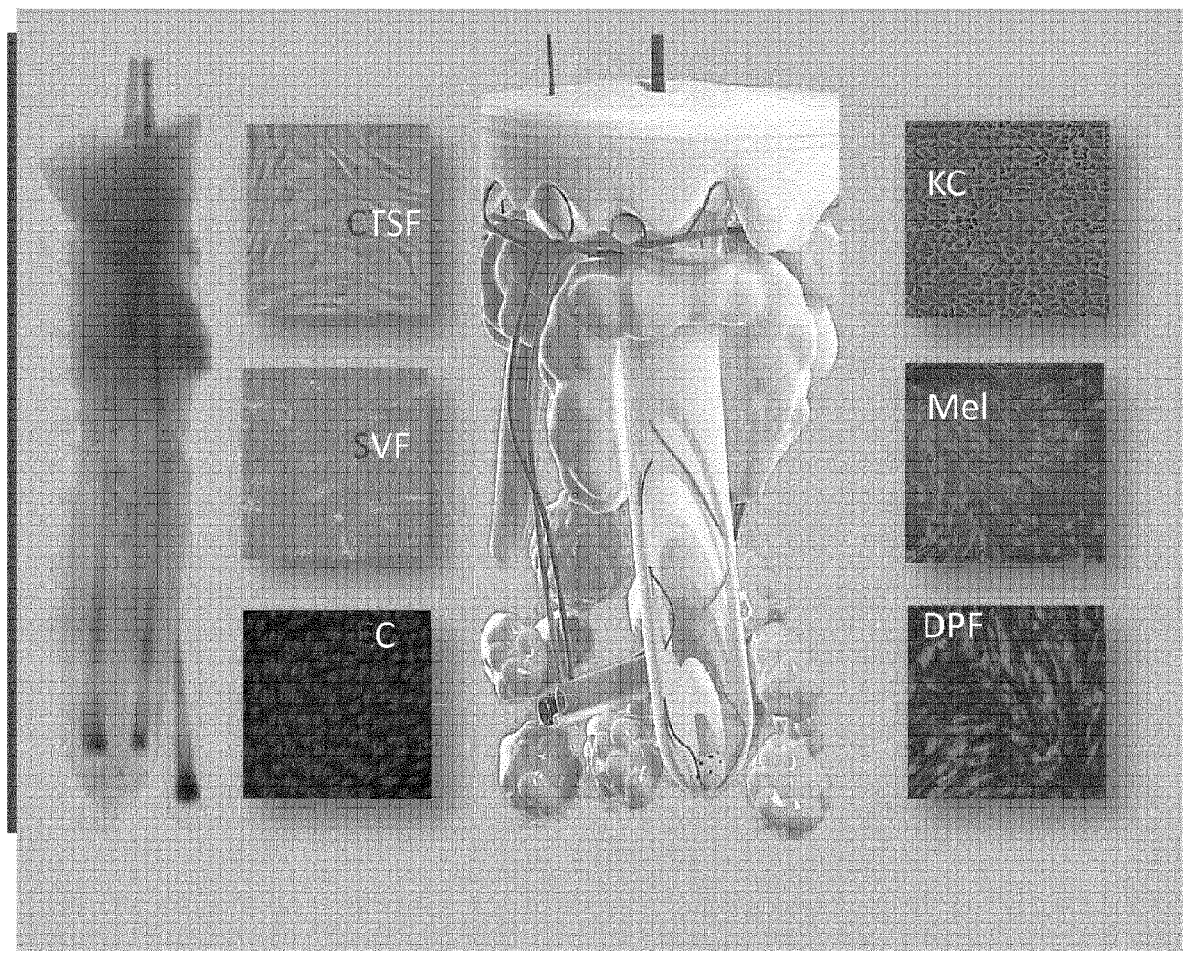

FIG. 2 shows:
A micrograph of a follicular unit and an illustrative drawing of the schematic structure of a follicular unit. The cells required for the de novo papillae and in vitro hair follicles can be isolated from the respective tissues. The FU substantially consists of the hair shaft, the epidermis, dermis, sebaceous gland, connective tissue sheath (CTS; CTSF), root sheaths (ORS, IRS; KC), sweat gland, blood vessels (endothelial cells), pigment unit (melanocytes), dermal papilla (DPF) and adipose tissue (adipocytes; SVF).

Figure 3:
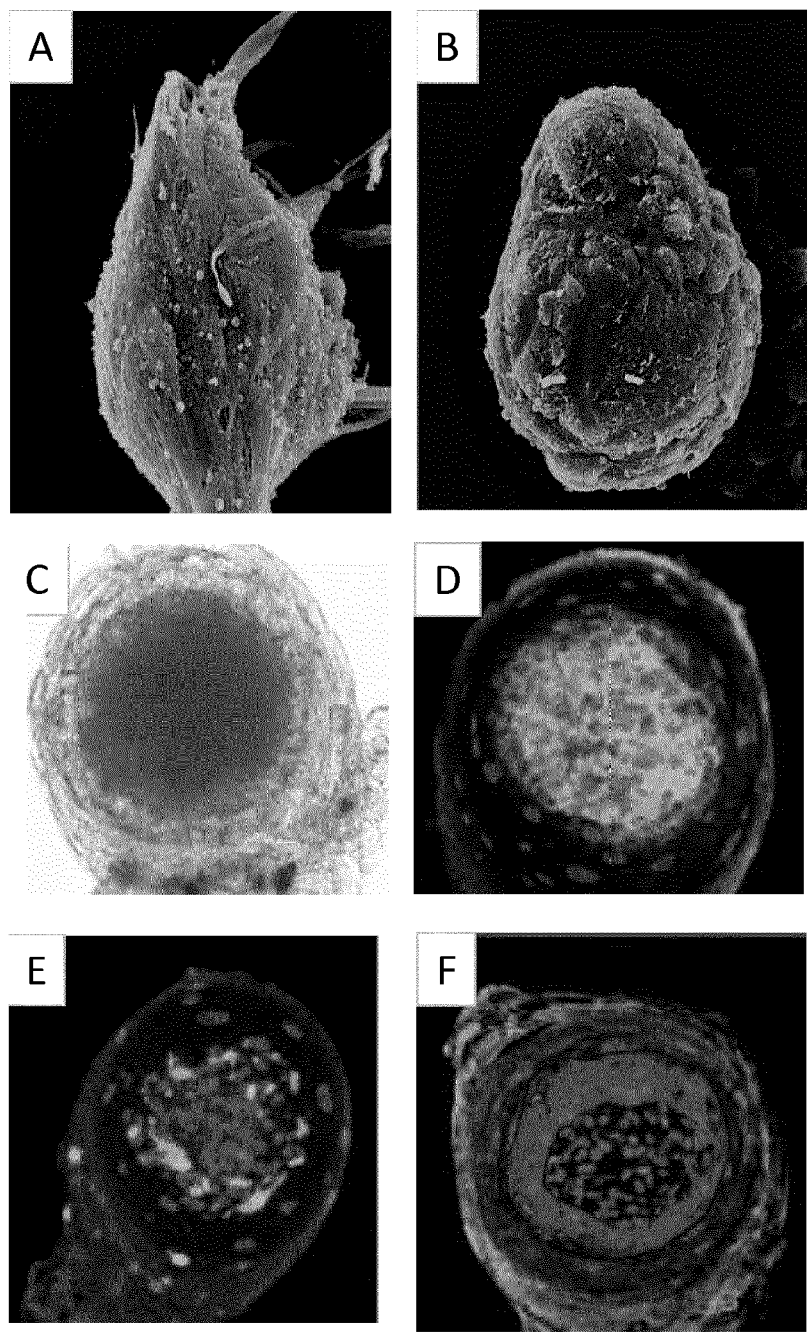

FIG. 3 shows:
A) A scanning electron micrograph of a dermal papilla after eversion and separation of the CTS.
B) A scanning electron micrograph of a de novo papilla generated from DPF and CTSF under non-adherent cell culture conditions.
C) An in vitro hair follicle consisting of a de novo papilla and surrounding keratinocytes and melanocytes which have formed an in vitro hair follicle in a non-adherent round-bottomed cavity of a multiwell cell culture plate. The polarization and differentiation of the surrounding keratinocyte layers are clearly visible. Pigment deposits (dark melanin granules) are also apparent.
D) A cryostat tissue section of an in vitro hair follicle which has been immunohistologically stained with a fluorescence marker for the DP-marking chondroitin 4-sulfate. Distinct compartmentalization of the DP (de novo papilla) and the surrounding epithelial (KC) cells is visible.
E) A cryostat tissue section of an in vitro hair follicle which has been immunohistologically stained with a fluorescence marker for the melanocyte-marking TRP1 protein. A uniform distribution of the pigment-forming melanocytes in the in vitro hair follicle compartments is apparent.
F) A cryostat tissue section of an in vitro hair follicle which has been immunohistologically double-stained with a fluorescence marker for keratin 15 (red) and keratin 10 (green). Differentiation of the keratinocytes surrounding the de novo papilla is visible, some of which have stem cell characteristics (K15 expression) while surrounding layers are already more differentiated (K10).

EXAMPLES

Example 1

Isolation of the Various Cell Types from Hair Follicles

DPF, CTSF, MC and KC were isolated from the human hair follicle in accordance with a modified form of the standard protocols (described for example in "Mager" et al."). Isolated hair follicles from punch biopsies or dissected hair follicles from an FUT hair transplantation were immobilized on the hair shaft with a pair of forceps and the connective tissue sheath was incised and diametrically separated therefrom carefully with another pair of forceps, so everting the bulb and exposing the dermal papilla and the hair shaft with the hair matrix. In this manner, the proximal part of the bulb with the connective tissue sheath fibroblasts and the dermal papilla could very easily be separated from the remainder of the hair follicle with the assistance of a needle/cannula. The hair shaft, which contains the hair matrix keratinocytes and melanocytes which are likewise required, was also optimally dissected for further culturing.

The dermal papillae and connective tissue envelopes extracted in this manner from the hair follicles which were taken were each collected in a separate vessel comprising medium. The DPF and CTSF were dissolved out and isolated from the surrounding tissue by gentle tissue dissociation using a tissue dissociator and the associated extraction kit (for example gentleMACS Dissociator #130-093-235, whole skin dissociation kit #130-101-540, Miltenyi Biotec). To this end, the isolated tissue fragments (dermal papilla, connective tissue envelope and hair shaft with epithelial/neuroectodermal cells), 435 µl buffer L, and an enzyme mix of 12.5 mg enzyme P and/or 4.50 mg enzyme D and/or 2.5 mg enzyme A were each introduced into a gentleMACS C tube and carefully mixed.

The sample was incubated in a water bath at 37° C. for 1-3 hours or overnight, longer incubation times increasing cell yield. After incubation, the sample was diluted by adding 0.5 ml cold cell culture medium. The C tube was sealed and fastened upside down onto the sleeve of the gentleMACS dissociator. The "h_skin_01" program was then run. Once the program was complete, a short centrifugation step was then carried out to collect the test material on the bottom. The cells could be washed with fresh medium and the cell suspension separated by a 70 µm filter. It is possible to dispense with the above-described addition of enzymes, which are undesirable in the case of direct autologous therapy, with the assistance of further dissociation runs, although in this case lower cell yields must be expected.

Example 2

Production of Cells from a Stromal Vascular Fraction (SVF)

A 1 liter fraction from tumescent liposuction of subcutaneous abdominal or hip fat was taken and prepared for example using the established PureGraft™ method (Cytori GmbH, Switzerland). This involved centrifugation and concentration in order to remove the tumescent solution. Digestion was then performed for 60 min at 37° C. in 0.15% (w/v) collagenase NB 6 GMP grade from *Clostridium histolyticum* (0.12 U/mg collagenase; SERVA Electrophoresis GmbH) diluted in phosphate-buffered saline (PBS; Gibco). After centrifugation at 180 g for 10 minutes, the lipid-rich layer was discarded and the cell pellet washed once with PBS. Erythrocytes were then dissolved by 2 minutes' incubation in lysis buffer (0.15 M ammonium chloride, Sigma-Aldrich). The stromal vascular fraction (SVF) obtained was suspended in complete medium (CM, Gibco).

Example 3

Production of Cells from the Outer Hair Root Sheath (ORS KC)

The corresponding region with head or beard hair was washed and disinfected (70% ethanol) and in each case 20-30 hairs were plucked with a rubber-coated pair of forceps. Only the hair with an adhering tissue layer was transferred into a vessel and rinsed in PBS. The hair was then incubated for 20 minutes at 37° C. in 2 ml trypsin/EDTA solution, after which it was briefly mixed with a shaker. The enzyme reaction was terminated with 4 ml trypsin inhibitor. Washing was performed with PBS and the suspension centrifuged at 200 g for 5 minutes. The cells could then be suspended in medium and used for further culturing or, after cell counting, for the remainder of the in vitro hair follicle production.

Example 4

Production of De Novo Papillae

1500 DPF and CTSF cells were pipetted into a cavity of a 384 ultra low attachment round bottom multiwell plate (Corning) (in DMEM+10% FCS and DermaLife medium in a 1:1 ratio) or were alternatively previously mixed with cells of the SVF or endothelial cells and then transferred into the cavities of the multiwell plate. The latter was centrifuged for 2 min at 200 g and incubated for 20 min at room temperature with rotating agitation at 20 rotations per minute. The medium was changed daily for longer culturing.

Example 5

Production of In Vitro Hair Follicles

A mixture of melanocytes and keratinocytes, which had been obtained by tissue dissociation from isolated or plucked hair shafts, were suspended in cell culture medium and in each case pipetted into the de novo papillae (15,000 cells/multiwell cavity). This suspension was centrifuged for 1 min at 200 g and incubated for 30 min at room temperature with rotating agitation at 20 rotations per minute. The medium was changed daily for longer culturing.

The invention claimed is:

1. A method for producing de novo papillae comprising the steps of:
   a) providing isolated dermal papilla fibroblasts (DPF) and isolated connective tissue sheath fibroblasts (CTSF) from at least one hair follicle;
   b) providing endothelial cells (EC) and/or cells of stromal vascular fractions (SVF); and
   c) co-culturing the DPF, CTSF, EC, and/or SVF under substantially non-adherent cell culture conditions to form spheroid cell aggregates.

2. The method according to claim 1, wherein the DPF and the CTSF are co-cultured in a ratio of 1-20:1-20.

3. The method according to claim 1, wherein the de novo papillae consist of 2 to 20000 cells.

4. The method according to claim 1, wherein the de novo papillae are coated with extracellular matrix proteins.

5. The method according to claim 1, wherein the co-culturing takes place with rotating, swiveling or shaking agitation.

6. The method according to claim 1, wherein the co-culturing takes place for at least 10 min.

7. A de novo papilla produced using the method according to claim 1.

8. A method for producing hair follicles comprising the steps of:
   a) providing at least one de novo papilla produced using the method according to claim 1;
   b) providing at least one further cell population selected from keratinocytes (KC), melanocytes (MC) or connective tissue sheath fibroblasts (CTSF); and
   c) co-culturing the de novo papilla with the at least one further cell population under substantially non-adherent cell culture conditions.

9. The method according to claim 8, wherein the de novo papilla is co-cultured with KC, MC and/or CTSF in a ratio of 1-10:1-50.

10. The method according to claim 8, wherein the at least one further cell population is obtained from a hair follicle.

11. The method according to claim 8, wherein the co-culturing takes place for at least 10 min.

12. A hair follicle produced using the method according to claim 8.

13. A skin equivalent comprising the de novo papilla according to claim 7.

14. A transplant comprising an effective amount of skin equivalent according to claim 13, optionally together with pharmaceutically acceptable adjuvants.

15. A skin equivalent comprising the hair follicle according to claim 12.

\* \* \* \* \*